United States Patent [19]

Hansen et al.

[11] 4,284,085

[45] Aug. 18, 1981

[54] ELECTRODE FOR IMPLANTATION INTO THE COCHLEA (II)

[76] Inventors: Carl C. Hansen, Sadolinsgade 114 B, DK-5000 Odense; Ole M. Lauridsen, Kaervej 13, DK-3520 Farum, both of Fed. Rep. of Germany

[21] Appl. No.: 959,756

[22] Filed: Nov. 13, 1978

[30] Foreign Application Priority Data

Nov. 22, 1977 [DK] Denmark .............................. 5167/77

[51] Int. Cl.$^3$ ................................................ A61N 1/04
[52] U.S. Cl. ................................. 128/784; 179/107 R
[58] Field of Search ................................ 128/784–786, 128/642, 789; 179/107 R, 107 B

[56] References Cited

U.S. PATENT DOCUMENTS

| | | | |
|---|---|---|---|
| 3,752,939 | 8/1973 | Bartz | 179/107 R |
| 3,890,977 | 6/1975 | Wilson | 128/785 X |

OTHER PUBLICATIONS

Sonn et al., "A Prototype Flexible Microelectrode...", Med. & Bio. Eng., Nov. 1974, pp. 778–790.

Primary Examiner—Lee S. Cohen
Attorney, Agent, or Firm—LeBlanc, Nolan, Shur & Nies

[57] ABSTRACT

An electrode for implantation into the cochlea. The purpose is to establish electrical communication to the acoustic nerves of the human ear, substantially in the area of the cochlea containing the acoustic nerves pertaining to that part of the audible spectrum, which is relevant to the intelligibility of speech. The problem is, that an electrode inserted into the cochlea certainly has made it possible to bring the patient in such a condition that she or he could interpret electrical signals supplied through the electrode as being sound but not as being intelligible speech.

The invention provides an electrode, which has two conditions of curvature, the one of which is temporary and corresponds to the curvature in the middle of the particular turn of the cochlea and the other one of which is permanent and corresponds to the first position of the electrode in the cochlea in which position it obtains an optimum contact to the acoustic nerves. The electrode of the invention further contains elements for changing the condition of curvature from the temporary one to the permanent one, when the electrode has been inserted into the cochlea. The permanent condition of curvature is constituted by the electrode's natural condition of curvature whereas the temporary condition of curvature is established by means of a detachable or loosenable connection, which, until it is detached or loosened, maintains the temporary condition of curvature. A quick and reliable operation is made possible and the probability of obtaining a uniform communication over various frequency ranges along the cochlea is greatly increased.

8 Claims, 8 Drawing Figures

ELECTRODE FOR IMPLANTATION INTO THE COCHLEA (II)

BACKGROUND OF THE INVENTION

The present invention is related to an electrode for implantation into the cochlea in order to establish electrical contact with the acoustic nerves of the human ear, the electrode comprises an insulating support member and supply lines to said nerves. Electrodes of this kind have been discussed by Martin Sonn. The prior art electrodes are disposed to be inserted through an opening to a patient's cochlea, whose internal ear is defective. In order to establish communication substantially in the area of the cochlea, which is relevant to the intelligibility of speech, the electrode is provided with an extension so that it can reach through approximately two of the cochlea's two and a half turns. It has appeared, however, that the purpose has not been attained, in as much as it has certainly been possible to bring the patient to such a condition that she or he could interpret electrical signals supplied through the electrode as being sound but not as being intelligible speech.

The present invention is based on the opinion that this phenomenon is partly due to the circumstance that the prior art electrode, which during the insertion had to be guided in the cochlea by the aid of the walls of the cochlea. During this insertion damage occurred to these walls. This resulted in the circumstance that the electrode, even if the insertion was tolerably successful, would not be able to position itself in the cochlea in such a manner that the supplied signals were conducted selectively to the acoustic nerves for which they were destined for evoking in the brain those impressions which could cause it to percept the electrical signals as communicating, intelligible speech.

SUMMARY OF THE INVENTION

The present invention aims at avoiding the drawbacks associated with the prior art electrode. Accordingly, the present invention provides an electrode having two conditions of curvature, the one of which is temporary and corresponds to the curvature of the middle of the particular turn of the cochlea, and the other one of which is permanent and corresponds to the final position of the electrode in the cochlea with the purpose of obtaining an optimum contact to the acoustic nerves, and prestressing means for changing the condition of curvature from the temporary one to the permanent one when the electrode has been inserted into the cochlea. By the term "temporary" is meant "reckoned to the time until the electrode has been inserted into the cochlea" and by the term "permanent" is meant "reckoned from the time after which the electrode has been inserted into cochlea". In this manner not only the possibility of a contactless insertion of the electrode into the cochlea is achieved so that its walls are not further damaged, but additionally the electrode, after being inserted into the desired turn or turns of the cochlea, can be given such a required, increased or decreased curvature, so that the electrode comes into contact with the internal or the external wall of the cochlea duct. The electrode is thereby designed to assume a constant position relative to the acoustic nerves throughout the various sections of the cochlea so that the nerve contacting electrodes of the electrode, through which the electrical signals have to be transmitted to the proper acoustic nerves, can obtain over the entire electrode a constant and an optimum position relative to the acoustic nerves.

By an embodiment of an electrode according to the present invention the permanent condition of curvature is constituted by the electrodes natural condition of curvature whereas the temporary condition of curvature is established by means of a detachable connection, which, until it is detached or loosened, maintains the prestressed temporary condition of curvature. The advantage of this embodiment is that the electrode, when it is inserted into the cochlea and when the detachable connection has been loosened, will be in a mechanically stressless condition, so that it is capable of assuming those delicate adjustments of the electrode normally made during the operation for insertion of the electrode, for a long time period without a tendancy to change. This then permits a quick and reliable operation, and that the probability of obtaining a uniform communication over various frequency ranges along the cochlea becomes larger.

In an embodiment of the electrode discussed above the mentioned detachable connection is thermo-detachable. Accordingly an elevation of temperature causes the detachable mechanical connection to be interrupted. Such heating can be carried out in many ways, for instance by diathermy, but it will be particularly advantageous if the thermo detachment is carried out at a temperature of a few degrees centigrade below the body temperature, because the electrode then, shortly after its insertion into the cochlea turn, will be heated by the surrounding tissue to a temperature above the critical temperature to cause the detachment so that the electrode by own efforts will finds its predetermined position in the cochlea. By way of specific example, this could happen if the detachable connection according to the invention is made of wax. By wax is to be understood in this connection not only organic waxes but also other materials having a similar softening temperature and being inert to body tissue and fluids in the surroundings mentioned.

In a modified embodiment of an electrode of the kind mentioned the detachable connection is made of a material soluble or swellable in a fluid. According to the invention such a fluid may be the lymph fluid in the cochlea. Also this embodiment provides an electrode which shortly after its insertion into the cochlea and without external influences assumes its predetermined position in the cochlea. Yet another possibility of having an electrode comprising detachable connections, which are soluble, is according to the invention constituted by the employment of a mucus, e.g. a mucus from the patient herself or himself, which mucus is in a dried condition. This too can be caused to loosen itself by its contact with the lymph fluid in the cochlea.

Further it is possible to provide an embodiment of the electrode according to the invention, in which the detachable connection is tearable. To this end it is necessary to employ mechanical forces, which in an embodiment of the electrode according to the invention are provided by the aid of a resilient hose inserted in the electrode, the hose containing a fluid, the pressure of which briefly can be increased to expand the hose and thereby tear up or break the detachable connection. Connections of this kind may be made by means of a light thermal welding, linear welding or spot welding involving a small weld area.

A particularly advantageous embodiment of an electrode according to the invention is obtained, if the detachable connection is positioned between two electrode surfaces, the one of which is carrying the electrode supply lines and the other one of which is carrying the nerve electrodes, and if said two surfaces are kept together along one of their longitudinal edges by means of an elastic connection formed by the insulating, supporting foil and along the other one of their longitudinal edges by means of said detachable connection. By this embodiment the surface including the electrode supply lines can be caused to lie inwardly or outwardly in the cochlea in a shape, which is roughly similar to a cylindrical surface. From this cylindrical surface the nerve electrodes can fold or unfold after the loosening of the detachable connection to establish contact with the partition in the cochlea, in which the acoustic nerves are situated thereby obtaining the closest contact to these nerves. In this embodiment it may be desirable that the surface carrying the nerve electrodes has in its free edge a number of V-shaped notches to facilitate the elastic unfolding of the nerve electrodes from the surface carrying the signal or supply lines.

Among the possible embodiments of an electrode according to the invention is another one by which the detachable connection is made up of a layer or a body on one or both sides of the insulating support member. This layer or body is applied to said member and is caused to become rigid, i.e. to harden or to solidify while the support member is forced to assume its temporary condition of curvature. After the insertion of the electrode into the cochlea the detachable connection is softened thereby causing the temporary condition of curvature to cease. This embodiment is extremely simple in manufacture and design and therefore causes only minor possibilities of fault.

As an alternative to electrodes having a detachable connection it is possible to make embodiments by which the curvature of the electrode is continuously variable and fixable in said two conditions of curvature. Electrodes of this kind can be manufactured uniformly and may even be adapted to widely varying working conditions, which may be of importance in various situations where it appears during an operation that special conditions exist such as cranial fractures or deformities, which require exceptional arrangements.

According to an embodiment of an electrode of this kind a cord is provided within or on the insulating support member, the length or the tightening of which cord adjusts the curvature of the electrode, and which cord is maintained temporarily in a condition, in which it causes the temporary condition of curvature.

By another embodiment of an electrode of such kind the insulating support member of the electrode is formed like a tube having an oval cross-section and containing a fluid, the pressure of which defines the condition of curvature of the tube. Advantages of such an electrode are, that it is extremely smooth and has a very little tendency to rupture the supply lines.

The invention will now be described in details below having reference to the accompanying drawings.

DESCRIPTION OF THE PREFERRED EMBODIMENTS

Figure 1:
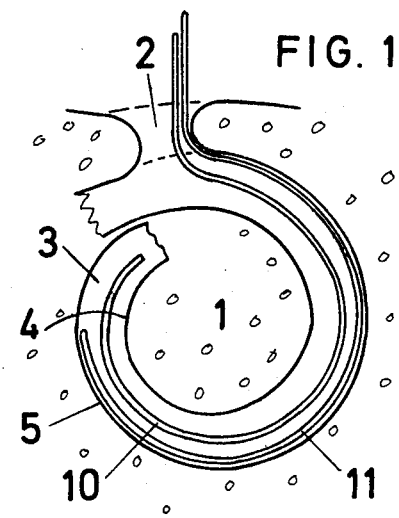
FIG. 1 is a projection of a section view through the center line in a single turn of a space in the cochlea during an operation for insertion of an electrode according to the invention.

In FIG. 1 reference numeral 1 indicates a section in the cranium, in which an opening 2 has been provided, which opening leads to a turn of the cochlea. This turn contains three spaces and normally one would introduce the electrode into the lower space 3. In the wall between said space and the intermediate one is the basilar membrane, and the acoustic nerves extend from the brain to the core of the cochlea and further to the field above the lower space. The lower space 3 has an internal wall 4 and an external wall 5 and forms a spiral. It is now possible to introduce the electrode according to the present invention through the opening 2. During the insertion the electrode has a curvature, which corresponds to the center line between the internal wall 4 and the external wall 5. This curvature is called "the temporary condition of curvature" 10. An electrode assuming the temporary condition of curvature 10 is in FIG. 1 illustrated immediately after its introduction. However, this position is not stable, as the electrode is floating, so to speak, in the lymph in the lower space. Therefore, a fixation of the electrode relative to the internal or external wall is important for enabling the current field between the nerve electrodes over the entire length of the electrode to contact accurately and uniformly the desired zones having nerve endings. Accordingly, the electrode of the present invention has a permanent condition of curvature 11, which may have either a smaller radius of curvature or, as illustrated in FIG. 1, a greater radius of curvature than the temporary one. Hence, the electrode will either nestle against the internal wall 4 or against the external wall 5 as shown in FIG. 1. Thereby, the electrode of the present invention has been given the combination of properties required for communication directly to the acoustic nerves: viz. it has to be so shaped that it can be introduced without damaging the walls of the cochlea and in such manner that it is fixed relative to the nerve endings uniformly over the entire length of the electrode. It can be said that apparently there is a discrepancy between the requirement of the two properties mentioned, but the discrepancy has been brought to a conclusion by the inventive realization of the necessity of an electrode having two conditions of curvature, a temporary one 10 and a permanent one 11.

Consequently, the electrode according to the invention must include means for changing the curvature from the temporary condition of curvature 10 to the permanent one 11. It is possible to have two types of such means as described herein.

When describing the first one of these two types of means, the term "natural condition of curvature" is employed. This means a curvature which an electrode will assume if it is not forced to assume another curvature, either as a result of an outer stress imposed by a band. For example, such a band can be disposed to straighten the electrode or even to give it a curvature of opposite direction. This can be done by temporarily giving the electrode internal stresses, which changes temporarily the natural condition of curvature. In case of the first mentioned type of means the internal stresses are maintained temporarily by the aid of a detachable connection. When said detachable connection is broken the electrode assumes its permanent condition of curvature, viz. its natural condition of curvature.

Figure 2:
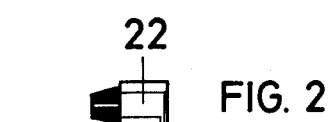
FIG. 2 is a plane, unfolded part of an embodiment of an electrode according to the invention.

In FIG. 2 is illustrated that part of the electrode according to the invention which carries the nerve electrodes 20 and which are to be positioned in cochlea. The remaining part of the electrode carries the connecting lines from the part illustrated to a signal generating apparatus. An electrode in this path of connections will usually have a base and a socket associated therewith permitting a separation between the patient and the signal apparatus. As neither the base, nor the socket nor the signal apparatus pertains the electrode according to the invention in another way than as necessary accessories, when the patient under operation is going to use the electrode, these parts have not been illustrated in the drawing and can be conventional types. The nerve electrodes 20 are arranged in pairs in a manner described in the inventor's copending application Ser. No. 959,757 and a conductor or supply line 21 leads to each nerve electrode. The nerve electrodes 20 as well as the conductor lines 21 are secured to an insulating support member 22 of a plastic foil having a suitable thickness, suitable properties of resilience and the property so that the foil is inert to body tissue and fluids, which also is required for the material of the nerve electrode and the conductor line. Conductor lines and electrodes can be applied on the foil by the aid of any known method such as by a thin film technique. The outline of the electrode is stamped out, cut out or punched out also by employing well-known techniques. Separating each pair of electrodes 20 there are contoured V-shaped notches 23 which protrude from one of the longitudinal edges. These notches serve to permit the required shape of double curvature, which the electrode must have in its temporary position as well as in its permanent position. Appropriately, the conductor lines 21 are covered by an insulating layer delimiting an external current field to the immediate proximity of the nerve electrodes 20.

Figure 3:
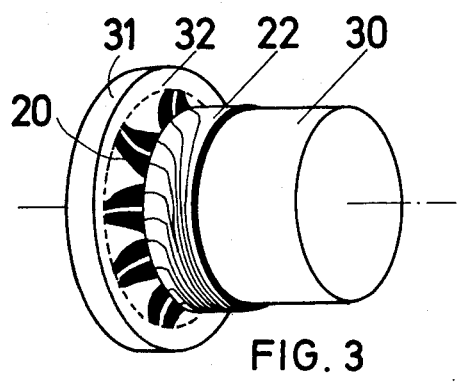
FIG. 3 is a schematic, perspective view of a form onto which an electrode is applied for setting a temporary condition of curvature according to the invention.

FIG. 3 illustrates a form or mandrel comprising two cylindrical members 30 and 31 respectively and therebetween a form member 32 of double curvature. The form of mandrel is disposed to be heated to a temperature above the softening temperature of the insulating support member 22. The form member 32 provides the same shape as the wall in the cochlea at the position of the permanent placement of the electrode. By placing the electrode so that its insulating support member 22 and nerve electrodes 20 are contacting the form member 32 and subsequently cooling the form or mandrel, from a temperature above the softening temperature to below the solidifying temperature, the electrode is caused to assume its natural condition of curvature. It is to be understood from FIG. 3 that the nerve electrodes and the conductor lines are facing the form or mandrel whereas the insulating support member is illustrated as being transparent. Then the electrode is seen from the back of the printed circuit connections.

Figure 4:
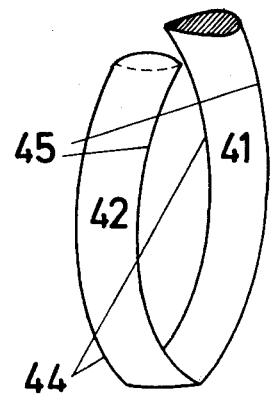
FIG. 4 is a schematic, perspective view of another form, around which an electrode according to the invention can be placed, while it is given a temporary condition of curvature.

Subsequently, an electrode fashioned as mentioned above is wrapped around another shaping member, which is illustrated in FIG. 4. This member is shaped like a flat ring, which is cut open and wrung a little out of plane so that its curvature corresponds to the temporary condition of curvature 10 illustrated in FIG. 1. Referring to FIG. 4, the cross-section of the ring is sharp-edged on the left-hand side 44 and round-edged on the right-hand side 45. The electrode is arranged on the "ring" with its back facing the ring and the nerve electrodes 20 folded into the in-side 41 of the ring whereas the conductor side is on the out-side 42 of the ring. The circumference of the cross-section of the ring is a little shorter than the distance between the edge 24 of the insulating support member and the tips 25 of the nerve electrodes 20. This has the effect that the electrode tips 25 will contact the edge 24 at the left-hand, sharp edge 44. It is at those contacts that the detachable connection is established in some of the embodiments of the invention.

As it appears from FIG. 4 the end of the ring, which is visible, has a little longer circumference than the other end, which is indicated partly in a dotted line. This design results in that the electrode can be pulled off the ring like a stocking after the detachable connections have been established.

By some of the embodiments the detachable connections are inserted between the edge 24 and the electrode tips 25 and by some other embodiments, in which use is made of wax or mucus, the detachable connections are best established by dipping or by spraying the connecting material while an auxiliary tool keeps the electrode members in position on the ring as discussed above, with reference to FIG. 4.

Figure 5:
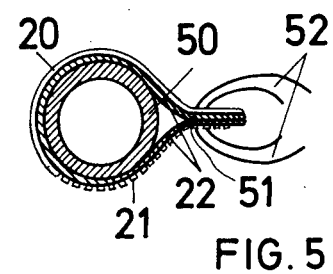
FIGS. 5 through 8 are cross-sections of further embodiments of an electrode according to the invention.

An embodiment, by which the detachable connection is tearable, is illustrated in FIG. 5. By this embodiment the electrode is folded around an elongated hose 50, which is accessible from the outside, instead of around the ring. The one end of the hose 50 is given a curvature similar to that of the ring. Then it is possible by means of a dot-welding tool 52 to provide tearable dot-weldings 51 between the nerve electrode side of the electrode and its conductor side and fairly close to the hose 50. This measure enables the hose 50 to tear up the dot-weldings by letting the hose expand resiliently by increasing the pressure in the interior of the hose.

Figure 6:
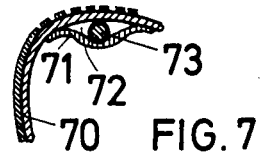

In this embodiment the temporary condition of curvature is provided to an electrode which has been given its permanent condition of curvature as described with reference to FIG. 3, by establishing a temporary condition of curvature 10 and in this condition a layer or a body 60, shown in FIG. 6 is applied. This layer or body has in itself a form stability which is sufficient to secure the temporary condition of curvature 10, but when the detachable connection is severed the nerve electrode side 20 is unfolded with the center part 61 of the electrode serving as an elastic hinge, the condition of curvature thereby altering to the permanent one 11.

Figure 7:
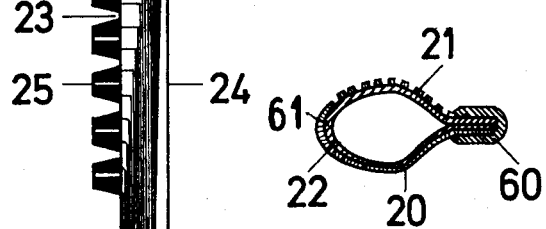

An embodiment of an electrode according to the invention can be given a continuously varying curvature if it is designed as indicated in FIG. 7. FIG. 7 is a cross-section of such an electrode in a direction orthogonal to its longitudinal axis. In this figure the thickness of the insulating support member 70 is, for the sake of clarity, shown very exaggerated. The section is illustrated when having its permanent shape. To the back of the printed circuit is attached a pocket 71 and in the cavity 72 of the pocket is inserted a cord 73, one end of which is secured to the tip of the electrode. When the cord is tightened by pulling its opposite free end the condition of curvature of the electrode could be increased in order to establish an arbitrary, required temporary condition of curvature. Having inserted such a curved electrode into the cochlea the pull of the cord is loosened whereby the electrode assumes its permanent curvature.

Figure 8:
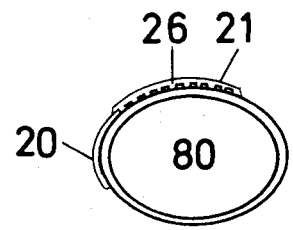

In FIG. 8 is illustrated a cross-section of an electrode shaped as a tube having an oval cross-section. The outer surface of this section carries nerve electrodes 20 and conductor lines 21 which are covered by an insulating layer 26. The electrode can by means of a thin film technique be provided on a thin foil, which subsequently is formed to a tube having a longitudinal seam, the tube can be arranged on a form or a mandrel of similar appearance as that illustrated in FIG. 4, but the sides 45 being rounded to the right-hand side as well as to the left-hand side. By heating to a temperature above the softening temperature of the foil and subsequently cooling to a temperature below the hardening temperature the tube 80 is given its natural condition of curvature 11. A temporary change of the pressure within the tube 80 will give the tube its temporary condition of curvature 10 for insertion into cochlea. This embodiment of the electrode according to the invention is particularly advantageous in that it is only subjected to negligible, mechanical influences when being inserted into cochlea so that the risk of rupturing the conductor lines is reduced.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. An implantable flexible electrode for implantation into the cochlea and disposed to establish electrical communication with the auditory nerves of the human ear, comprising: an elongate foil-like support member of a flexible electrically insulating material; a pattern of electrically conductive paths of a material inert to body fluids and tissue applied to a planar surface of said support member, said pattern extending along said planar surface and terminating each of said paths in an enlarged exposed contact area, and wherein the part of the support member to be accommodated in the cochlea has a natural curvature in the longitudinal direction of the support member which corresponds to the curvature of the cochlea wall containing the nerve endings in the particular turn of the cochlea into which it is to be inserted; means for releasably prestressing said support member to attain a temporary curvature to facilitate insertion into the middle of said turn of the cochlea; said prestressing means being capable of being released when the curved support member is secured in place in the particular cochlea turn to permit said member to return to its natural curvature condition to establish optimum engagment between the nerve endings and the exposed electrode contact areas.

2. An implantable electrode according to claim 1, wherein said prestressing means is formed at least in part from a material releasable by interaction with body fluid or heat.

3. An implantable electrode according to claim 2, wherein said prestressing means comprises a material selected from the group consisting of a dried mucus and a body heat softenable wax which retains said support member in its temporary curvature condition.

4. An implantable electrode according to claim 1, wherein said prestressing means comprises tearable mechanical connections formed between contacting portions of said flexible electrically insulating material when said support member is in the prestressed condition.

5. An implantable electrode according to claim 8, wherein said flexible support member is folded laterally around a resilient hose containing a pressurized fluid and shaped to conform to the temporary curvature, and said hose being adapted to increase in diameter briefly by increasing the pressure in the contained fluid to enable severing of said mechanical connections.

6. An implantable electrode according to claim 1 wherein the curvature of the support member is continuously variable and is fixable in said two conditions of curvature.

7. An implantable electrode according to claim 1, wherein said prestressing means comprises a tightenable cord secured by one end thereof to said support member and disposed along the longitudinal direction thereof, so that tension exerted along said cord maintains the condition of temporary curvature of said support member part to be inserted into the cochlea.

8. An implantable electrode according to claim 1, wherein said support member is constructed in the form of a tube having an oval cross-section and a natural curvature in a longitudinal direction thereof, and wherein said prestressing means comprises a pressure medium contained within said tube in which the pressure can be increased to enable said tube to be prestressed to a temporary curvature for insertion into the cochlea.

* * * * *

UNITED STATES PATENT AND TRADEMARK OFFICE
CERTIFICATE OF CORRECTION

PATENT NO. : 4,284,085
DATED : August 18, 1981
INVENTOR(S) : Carl Christian Hansen & Ole Mork Lauridsen It is certified that error appears in the above-identified patent and that said Letters Patent are hereby corrected as shown below:

Column 8, line 24, change "claim 8," to --claim 4,--

Signed and Sealed this

Eighth Day of December 1981

[SEAL]

Attest:

GERALD J. MOSSINGHOFF

*Attesting Officer*  *Commissioner of Patents and Trademarks*